(12) United States Patent
Kawaguchi et al.

(10) Patent No.: US 6,213,888 B1
(45) Date of Patent: Apr. 10, 2001

(54) GOLF CLUB SHAFT

(75) Inventors: Masatake Kawaguchi; Makoto Watari; Katsumi Shimohira; Atsushi Yagita, all of Kanagawa (JP)

(73) Assignee: Nippon Shaft Co., Ltd. (JP)

( * ) Notice: Subject to any disclaimer, the term of this patent is extended or adjusted under 35 U.S.C. 154(b) by 0 days.

(21) Appl. No.: 09/252,446

(22) Filed: Feb. 18, 1999

(30) Foreign Application Priority Data

Sep. 7, 1998 (JP) .................................................. 10-267235

(51) Int. Cl.$^7$ .......................... A63B 53/10; A63B 53/12; G01N 3/22; G01N 3/20
(52) U.S. Cl. .......................... 473/223; 473/409; 73/847; 73/849
(58) Field of Search .................................. 473/223, 409; 73/65.03, 650, 763, 767, 847, 849

(56) References Cited

U.S. PATENT DOCUMENTS

| | | | |
|---|---|---|---|
| 3,270,564 | * | 9/1966 | Evans . |
| 3,792,863 | * | 2/1974 | Evans . |
| 3,806,131 | * | 4/1974 | Evans . |
| 3,945,646 | * | 3/1976 | Hammond . |
| 4,157,181 | * | 6/1979 | Cecka . |
| 5,792,000 | * | 8/1998 | Weber ................................. 473/223 |
| 5,821,417 | * | 10/1998 | Naruo ................................. 473/223 |
| 5,947,839 | * | 9/1999 | Kusumoto ........................... 473/319 |

FOREIGN PATENT DOCUMENTS 10244023  9/1998 (JP) .

OTHER PUBLICATIONS

M. Watari, et al., "Studies on Golf Swing Type and Matching Golf Club to the Player", presented at the World Scientific Congress of Golf, University of St. Andrews, Scotland, Jul. 20–24, 1998, 1 page.

Nippon Shaft, "Studies on Golf Swing Type and Matching Golf Club to the Player", presented at the World Scientific Congress of Golf, University of St. Andrews, Scotland, Jul. 20–24, 1998, pp. 2–10.

* cited by examiner

Primary Examiner—Jeanette Chapman
Assistant Examiner—Stephen L. Blau
(74) Attorney, Agent, or Firm—Ostrolenk, Faber, Gerb & Soffen, LLP

(57) ABSTRACT

A golf club shaft includes a first strain gauge attached to a first side of the shaft facing the striking direction, a second strain gauge attached to a second side of the shaft facing the address direction at right-angles to the striking direction, and a third strain gauge which is capable of measuring the twist of the shaft. Detection signals from the strain gauges are used to classify a shaft into four types according to the swing type of a golfer in accordance with at least torque or kick point.

24 Claims, 14 Drawing Sheets

| | TORQUE(°) | KICK POINT (%) | FLEX (mm) |
|---|---|---|---|
| I | 5.8 (5.6~7.2) | 40.0 (38~42) | A,R1,R2,S1,S2,X |
| P | 4.8 (4.6~5.0) | 41.5 (40~43) | ″ |
| D | 4.2 (4.0~4.4) | 43.0 (42~45) | ″ |
| J | 3.6 (3.4~3.8) | 44.5 (44~47) | ″ |

(TYPES OF SWING)
(ADDRESS WAGGLE OMITTED)

Fig.13

|   | TORQUE | KICK POINT |
|---|--------|------------|
| I | GREAT  | TIP        |
| P | :      | :          |
| D | :      | :          |
| J | SMALL  | BUTT       |

Fig.14

|   | TORQUE(°)    | KICK POINT (%) | FLEX (mm)         |
|---|--------------|----------------|-------------------|
| I | 5.8 (5.6~7.2)| 40.0(38~42)    | A,R1,R2,S1,S2,X   |
| P | 4.8 (4.6~5.0)| 41.5(40~43)    | ″                 |
| D | 4.2 (4.0~4.4)| 43.0(42~45)    | ″                 |
| J | 3.6 (3.4~3.8)| 44.5(44~47)    | ″                 |

Fig.15

| A   | R1  | R2  | S1  | S2  | X   |
|-----|-----|-----|-----|-----|-----|
| 150 | 133 | 132 | 126 | 120 | 112 |

(± 3)

MARUMAN GOLF KK JGGA-APPROVED TORQUE MEASUREMENT TESTING APPARATUS
TORQUE [°/ft-lb]

MEASUREMENT POINT

THIS COMPANY'S BEND POINT TESTING APPRATUS
(KICK POINT MEASUREMENT TESTING APPARATUS)
KICK POINT KP=L2/L1×100 [%]

| L | A |
|---|---|
| 46" (1168mm) | 128mm |
| 45" (1143mm) | 103mm |
| 44" (1118mm) | 78mm |
| 43" (1092mm) | 52mm |
| 42" (1067mm) | 27mm |

THIS COMPANY'S JGGA-APPROVED FLEX
MEASUREMENT TESTING APPARATUS

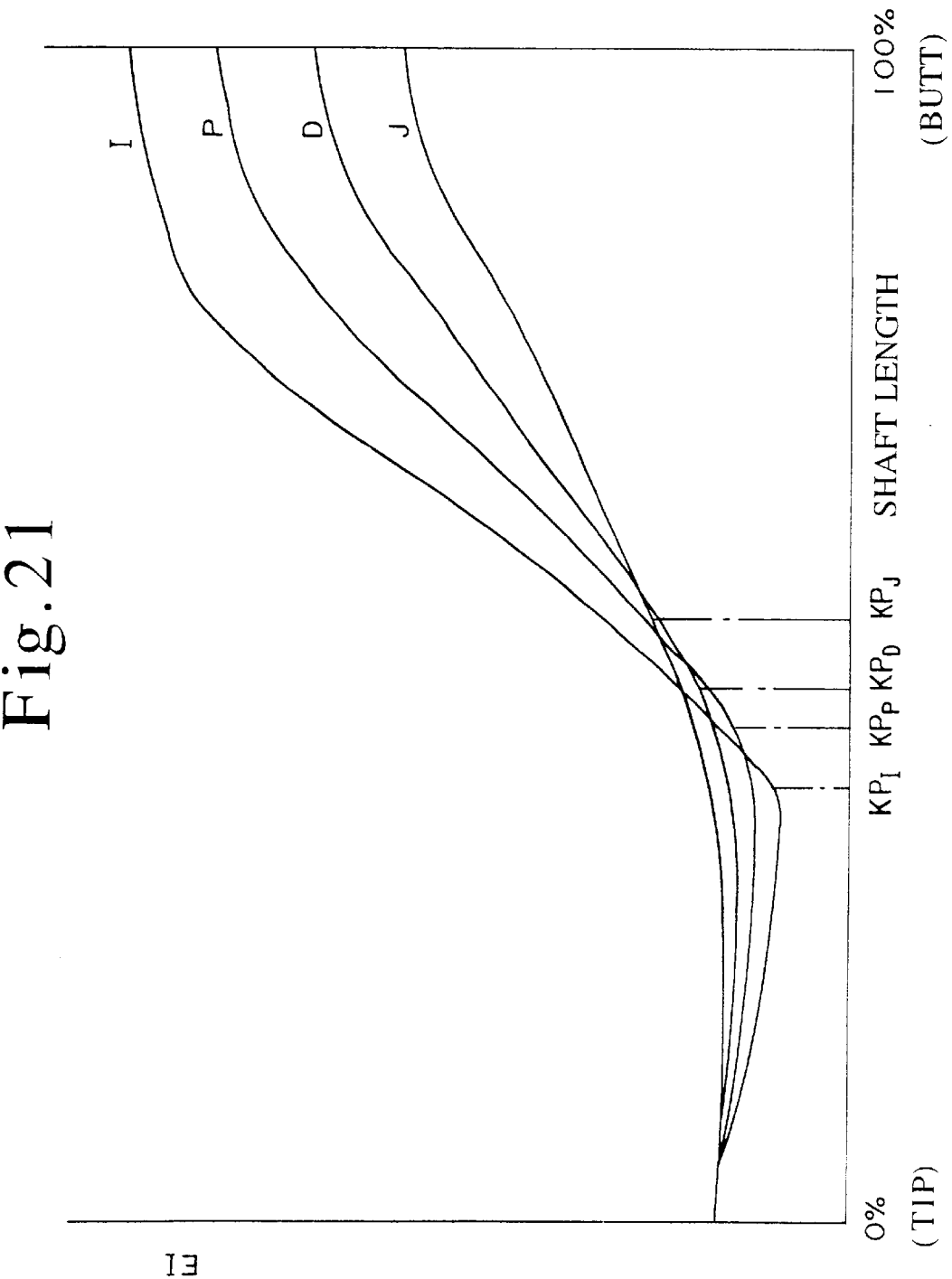

GOLF CLUB SHAFT

BACKGROUND OF THE INVENTION

1. Field of the Invention

The present invention relates to a golf club shaft, and in particular to a golf club shaft which adapts to the characteristics (type) of a golfer's swing.

2. Description of the Related Art

When selecting golf clubs to suit each golfer, the conventional method has been to do so by feel as a result of actually swinging several different clubs, but the question remains that it is not clear if the judgement is a correct one or not.

Meanwhile, it is normal to choose a fairly pliable golf club shaft for a beginner or for a woman, and a relatively hard one for a professional or a golfer with a powerful stroke. There is an element of preference, and it is often impossible to generalize, but again the disadvantage is that the selection has had to be based on feel.

What is more, there is also a problem in that there has been no objective means of grasping the characteristics of each golfer's swing as such for the purpose of practicing, correcting or improving swing technique, and it has been necessary to rely on subjective or empirical criteria.

It is true that there are methods of detecting the bending strain (stress) which accompanies a swing by attaching a strain gauge to the grip section of the golf club, thus monitoring the degree of force which comes into play as the result of a swing. However, this method of detection consists simply of attaching a single strain gauge, which not only makes it difficult to grasp a golf swing objectively, but also extremely difficult to select a golf club or golf club shaft to suit each golfer.

In view of the foregoing problems, it is an object of the present invention, having analyzed golf swings objectively, to provide a golf club shaft can be selected in accordance with the swing of each golfer.

It is a further object of the present invention to classify golfers' swings into four types, and to provide a golf club shaft which allows the club most suited to each golfer to be prepared.

It is yet a further object of the present invention to provide a golf club shaft which permits quantizing the differences between the four types of club, so as to allow the club most suited to each golfer to be prepared.

SUMMARY OF THE INVENTION

The inventors of the present invention have noticed that irrespective of whether they are beginners, intermediates or professionals, or which sex they belong to, golfers' swings can be classified into four types (I type, P type, D type and J type), and that these four types can be classified according to specific physical quantities, namely torque and kick point as measured with the aid of the third strain gauge. Accordingly, the present invention is a golf club shaft wherein are provided a first strain gauge attached to a first side of the shaft facing the striking direction, a second strain gauge attached to a second side of the shaft facing the address direction at right-angles to the striking direction, and a third strain gauge which is capable of measuring the twist of the shaft, detection signals from these gauges being used to classify the shaft into four types according to the swing type of each golfer, these four types of shaft being specified in accordance at least with either torque or kick point.

The abovementioned four shafts may be termed the I-type shaft, P-type shaft, D-type shaft and J-type shaft.

The abovementioned torque can be reduced gradually in order from the I-type shaft through the P-type shaft and the D-type shaft to the J-type shaft.

The abovementioned kick point can be increased gradually in order from the I-type shaft through the P-type shaft and the D-type shaft to the J-type shaft.

The abovementioned torque can be set in the case of the I-type shaft at between 5.6° and 7.2°, preferably 5.8°, in the case of the P-type shaft at between 4.6° and 5.0°, preferably 4.8°, in the case of the D-type shaft at between 4.0° and 4.4°, preferably 4.2°, and in the case of the J-type shaft at between 3.4° and 3.8°, preferably 3.6°.

The abovementioned kick point can be set in the case of the I-type shaft at between 38% and 42%, preferably 40%, in the case of the P-type shaft at between 40% and 43%, preferably 41.5%, in the case of the D-type shaft at between 42% and 45%, preferably 43%, and in the case of the J-type shaft at between 44% and 47%, preferably 44.5%.

It is possible to ensure that if $T_i$ (where i=the I-type shaft, the P-type shaft, the D-type shaft and the J-type shaft) represents the torque, M represents a value in the striking direction or in the direction at right-angles to the striking direction, whichever is the greater, based on the detection signals from the first and second strain gauges, c is a constant, and $d_i$ is a constant for each type, the formula $T_i = 1/(c \cdot M + d_i)$ obtains.

It is possible to ensure that if $KP_i$ (where i=the I-type shaft, the P-type shaft, the D-type shaft and the J-type shaft) represents the kick point, $T_i$ represents the torque for each type, and e, f and g are constants, the formula $KP_i = e \cdot T_i^2 + f \cdot T_i + g$ obtains.

It is possible for the abovementioned shaft to be manufactured from carbon fiber reinforced plastics or glass fiber reinforced plastics.

It should be added that the classification of the abovementioned golf club shafts into four types has proven that, contrary to conventional belief or conjecture, there is no connection with the flex of the shaft.

In other words, the characteristics of each golfer's swing type can be depicted graphically by representing the degree of strain (strain stress) in the horizontal direction (striking direction, H axis) and that in the vertical direction (direction at right-angles to the striking direction, V axis) during the action of swing as rectangular coordinates (H-V diagram). By analyzing the degree of twist and swing time in addition to the abovementioned strain stress, it is aimed to render the swings of individual golfers into patterns, and to provide a type of golf shaft suited to each of these patterns.

The golf club shaft to which the present invention pertains is classified by torque and kick point values in accordance with patterns measured and analysed from golfers' swings. Once the swing type of each golfer is classified, it is possible immediately to recommend or select a shaft suited to that golfer's swing.

In particular, the fact that four types are specified on the basis of torque and kick point makes it possible to select objectively and swiftly a shaft which is suited to each golfer and easy to swing, rather than relying on feel as hitherto.

BRIEF DESCRIPTION OF THE DRAWINGS

FIG. 13 is a table illustrating the relationship between golf club shafts for use by the various types (I type, P type, D type and J type) on the one hand, and torque and kick point on the other in the golf club shaft to which the present invention pertains;

FIG. 14 is a table illustrating in the form of concrete figures the relationship between golf club shafts for use by the various types (I type, P type, D type and J type) on the one hand, and torque, kick point and flex on the other in the golf club shaft to which the present invention pertains;

FIG. 15 is a table showing concrete figures for flex in the golf club shaft to which the present invention pertains;

FIG. 21 is a graph showing EI distribution against the length of the golf club shaft 50 to which the present invention pertains.

DESCRIPTION OF THE PREFERRED EMBODIMENTS

There follows, with reference to FIGS. 1–21, a description of the preferred embodiments of the present invention.

As a preliminary step and pre-condition for selecting the golf club shaft to which the present invention pertains, the golf swing analyzer 1, the method of analysis it employs, and the golf club 2 will be described with reference to FIGS. 1–7 (cf. Japanese Patent Application H7[1995]-69037 (Publication No. H10 (1998)-244023)).

Figure 1:
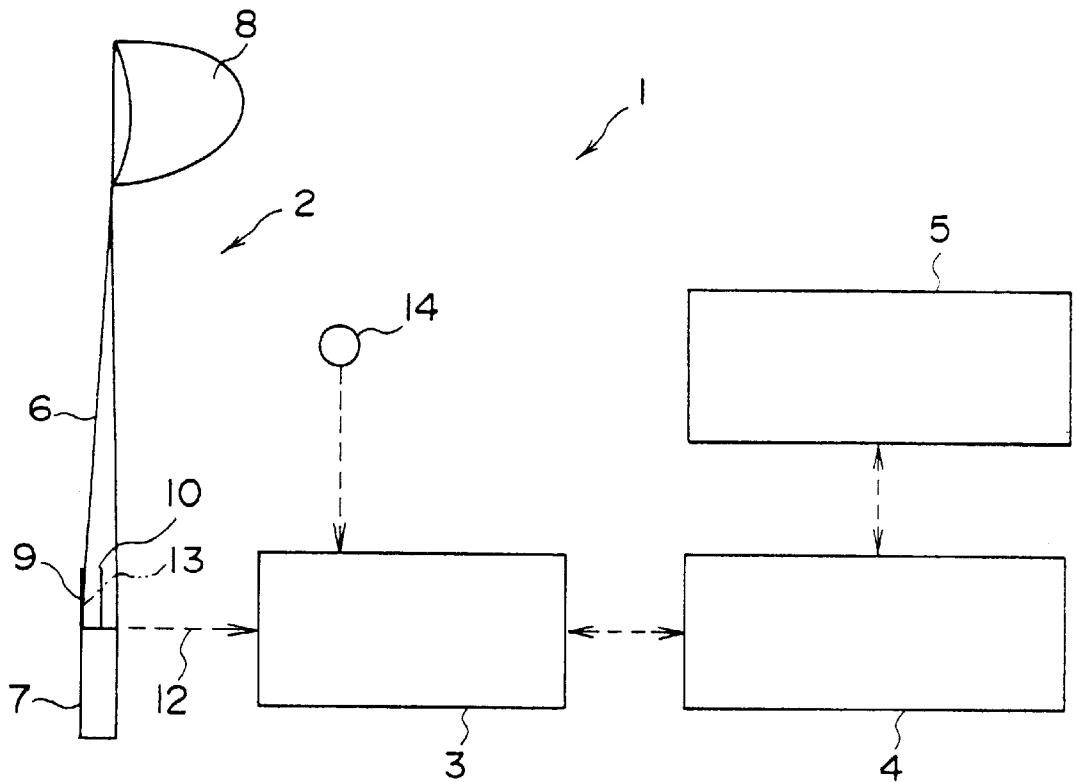
FIG. 1 is an outline explanatory drawing illustrating the golf swing analyzer 1 according to the present applicant's Japanese Patent Application H7[1995]-69037 (Publication No. H10(1998)-244023)

FIG. 1 is an outline explanatory drawing illustrating the golf swing analyzer 1. The golf swing analyzer 1 comprises a golf club 2, a swing analysis circuit 3 (means of swing analysis), a personal computer 4, and a printer 5.

The golf club 2 has a shaft 6, a grip 7 and a club head 8. A first strain gauge 9 and a second strain gauge 10 are attached in the vicinity of the grip 7 (e.g. on the butt side of the grip).

The first strain gauge 9 is attached to the side facing the striking direction (the left-hand side in FIG. 1), while the second strain gauge 10 is attached to the side facing the address direction at right-angles to the striking direction (the center in FIG. 1).

Figure 2:
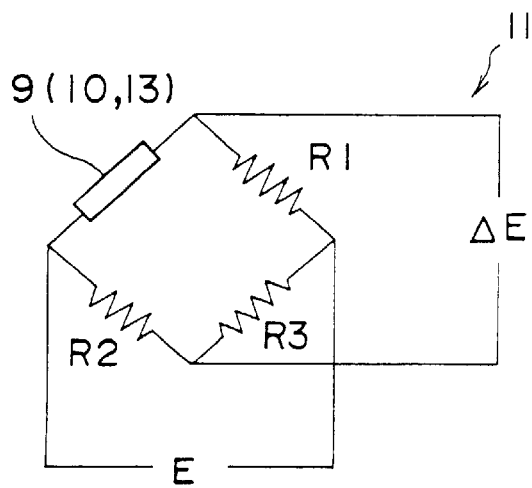
FIG. 2 is an outline diagram illustrating an example of the strain detection bridge circuit 11 within the swing analysis circuit 3 of the abovementioned golf swing analyzer 1 (one-gauge method)

FIG. 2 is an outline diagram illustrating an example of the strain detection bridge circuit 11 within the swing analysis circuit 3 of the abovementioned golf swing analyzer 1 (one-gauge method). The first strain gauge 9 and second strain gauge 10 are loaded with constant voltage E, as are the constant resistance R1, R2 and R3. This makes it possible to obtain changes in voltage ΔE (detected voltage) proportionate to the elongation (tensile strain) and contraction (compressive strain) following the swing of the golf club 2. Stress can be calculated by multiplying this detected voltage by the modulus of longitudinal elasticity. A two-gauge method or a four-gauge method can also be employed.

Figure 3:
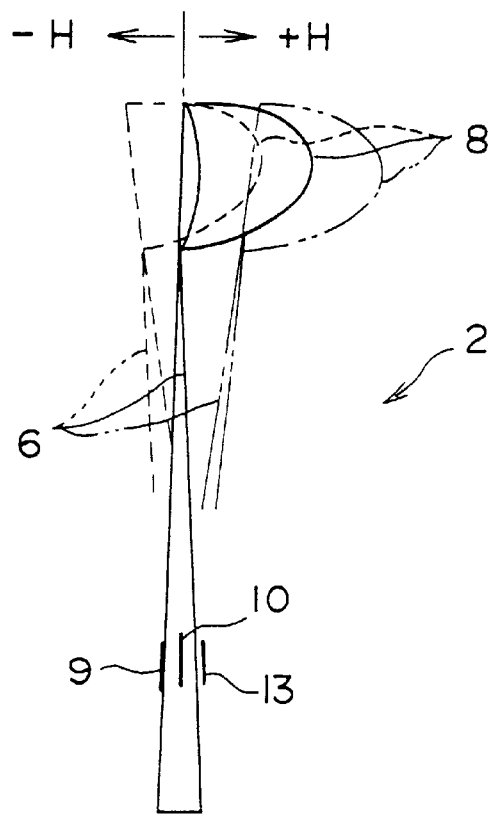
FIG. 3 is an outline diagram illustrating distortion to the shaft 6 resulting from a swing, and the action of detecting (in the H direction) by the first strain gauge 9 of the abovementioned golf swing analyzer 1.
Figure 4:
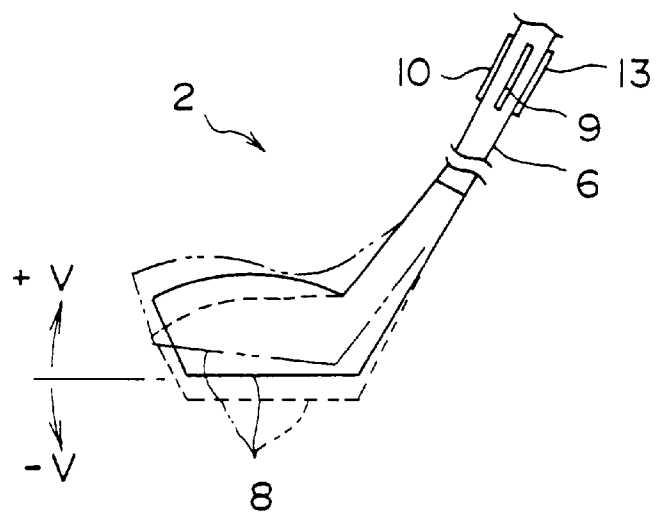
FIG. 4 is an outline diagram illustrating distortion to the shaft 6 resulting from a swing, and the action of detecting (in the V direction) by the second strain gauge 10 of the abovementioned golf swing analyzer 1.

FIGS. 3 and 4 are outline diagrams illustrating distortion to the golf club 2, and particularly to the shaft 6, resulting from a swing, and the action of detecting (in the H direction) by the first strain gauge 9 and second strain gauge 10 respectively of the abovementioned golf swing analyzer 1. As FIG. 3 demonstrates, if as a result of a swing of the golf club 2 within a plane which includes the striking direction the club head 8 bends backwards in the striking direction from the axis of the shaft 6 (so that the club head 8 is to the right of the axis of the shaft 6), the bending strain is +H. If it bends forwards in the striking direction (so that the club head 8 is to the left of the axis of the shaft 6), the bending strain is −H.

As FIG. 4 demonstrates, if as a result of a swing of the golf club 2 within a plane which includes the address direction at right-angles to the striking direction the club head 8 bends upwards from the axis of the shaft 6, the bending strain is +V. If it bends downwards from the axis of the shaft 6, the bending strain is −V.

In other words, the detected bending strain shows the direction in which the club head 8 bends in relation to the grip position.

It should be added that as far as the actions of the person making the swing is concerned, basically speaking the action of using the hands is detected as strain on the V axis, while that of turning the body is detected as strain on the H axis.

On the basis of detection signals from the first strain gauge 9 and second strain gauge 10, the swing analysis circuit 3 synthesises and represents graphically the strains H and V in the striking and address directions respectively.

The personal computer 4 controls the whole golf swing analyzer 1, and on the basis of signals from the swing analysis circuit 3 prints output diagrams or graphs on the printer 5.

The first strain gauge 9 and second strain gauge 10 on the one hand and the swing analysis circuit 3 on the other are connected by connecting cable 12, which is long enough to allow a swing to be implemented satisfactorily.

The golf club 2 may be one provided for that purpose, or if the golfer wishes to try swinging his own or a specific golf club 2, the first strain gauge 9 and second strain gauge 10 (along with the third strain gauge 13 described below) may be attached to that golf club 2.

The first strain gauge 9 and second strain gauge 10 serve to measure the strain H, the strain V and the swing time, while the head speed is measured with the aid of a speedometer 14. A third strain gauge 13 is attached in the vicinity of the grip 7 of the golf club 2 in the same manner as the first strain gauge 9 and second strain gauge 10, except that it is attached diagonally (at 45°) in line with the twist direction of the shaft 6.

This third strain gauge 13 serves to detect the twist torque around the shaft 6 following a swing. Data concerning this twist torque is linked with movement in the twist direction of the shaft 6 as viewed from the grip 7 (the clockwise direction being plus), namely the direction in which the club head 8 faces.

This being the structure of the golf swing analyzer 1, the golfer whose swing it is wished to analyze grips the golf club 2 and executes a swing.

Figure 5:
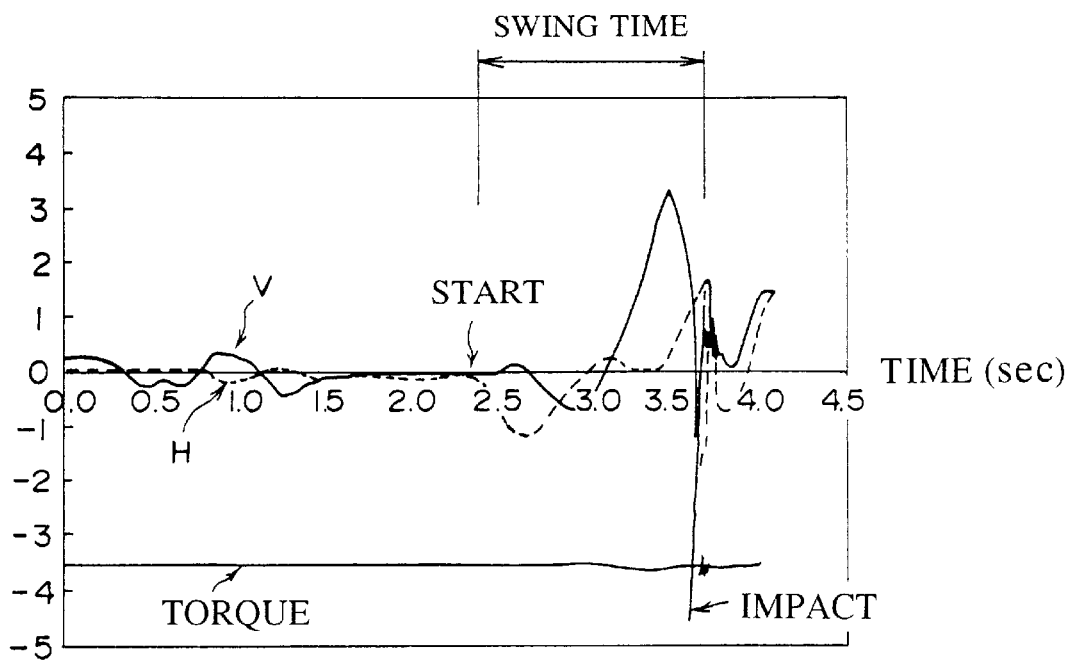
FIG. 5 is a graph depicting temporal changes in detection results due to a swing in the abovementioned golf swing analyzer 1.

FIG. 5 is a graph depicting temporal changes in detection results due to a swing in the abovementioned golf swing analyzer 1.

In the graph, the broken line represents strain in the H direction following the swing, while the unbroken line represents strain in the V direction. The lower part of the graph represents the twist torque, and it is possible to analyse the action and timing from address to impact.

Figure 6:
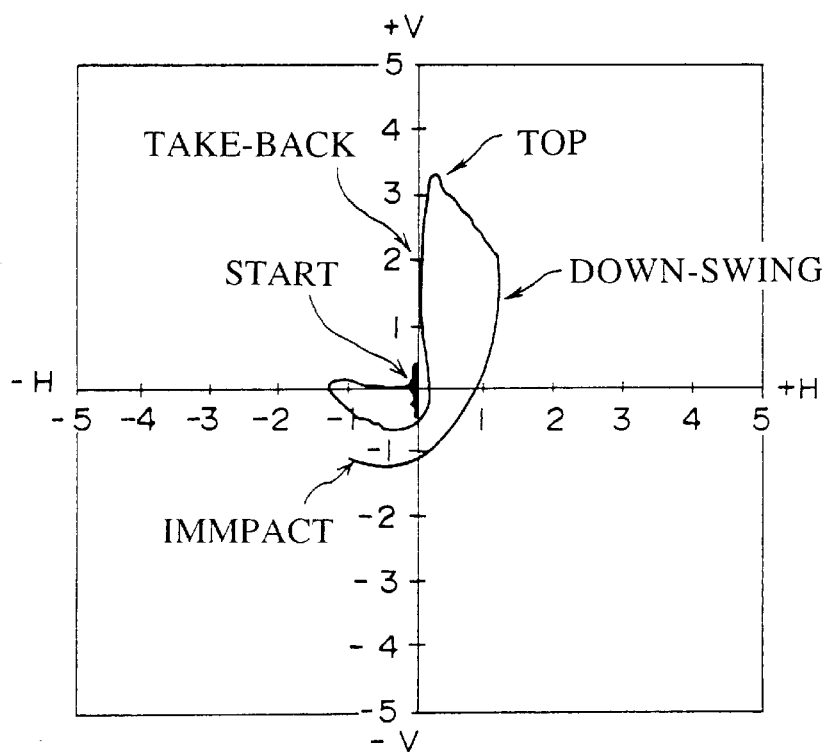
FIG. 6 is an H-V graph illustrating an example of measurement of a certain golfer's swing in the abovementioned golf swing analyzer 1.

FIG. 6 is an H-V graph illustrating an example of measurement of a certain golfer's swing. It is based on detection signals from the first strain gauge 9 and second strain gauge 10, the swing analysis circuit having depicted graphically the respective strains in the striking (H) and address (V) directions on rectilinear coordinates in the form of an H-V graph.

As FIGS. 5 and 6 show, it is possible to measure bending strain from commencement of the swing through take-back, top position and down-swing to impact, representing the characteristics of the swing as a pattern on a two-dimensional H-V graph.

The swing itself differs between golfers, but in general outline terms when the back-swing is initiated after the address, the V strain increases in the plus direction. Once the down-stroke is entered from the top position, the H strain increases in the plus direction, while the V strain decreases, both H strain and V strain becoming minus at the moment of impact.

To be more precise, If a golfer keeps the club head 8 off the ground in the address state, strain is generated in the −V direction. If the club head 8 is rested on the ground, the strain generated is either zero or in the +V direction.

Moving the club head 8 from the address to the take-back state causes strain to be generated temporarily in the −H direction as a result of the force of inertia of the club head 8. Strain is generated in the −V direction when the golf club 2 is raised either with the hand of by virtue of a body-turn.

In the case of a square grip, strain is generated in the +V direction in the top state because in the top position the thumb of the left hand becomes the fulcrum. If cocking is early, the strain in the +V direction generated in the top position is relatively small. If the top position is shallow, the strain in the +V direction generated there is very small, and may also be in the −V direction. If the top position is deep, the strain in the +V direction generated in the top position is great. In the case of an over-swing, strain in the −H direction is generated in the top position.

The inventors of the present invention have carried out measurements on a large number of golfers, and have found that their H-V graphs can be broadly divided into four types, which they have called I type, P type, D type and J type.

Figure 7:
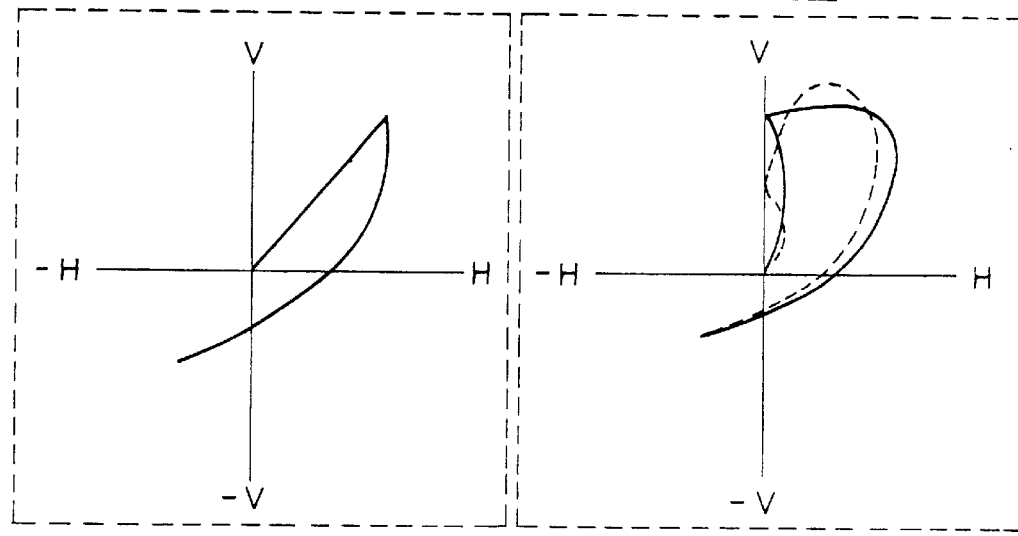
FIG. 7 depicts simultaneously I-type, P-type, D-type and J-type H-V graphs in the abovementioned golf swing analyzer 1.

FIG. 7 depicts simultaneously I-type, P-type, D-type and J-type H-V graphs. The I type has a uniaxial pattern, the P type and D type have a biaxial pattern, and the J type has a triaxial pattern.

As far as swing type tendencies are concerned, the I type and P type are wrist-turn, draw-type hitters, while the D type and J type are no wrist-turn, fade-type hitters. The I type and J type utilise the rebound of the golf club 2 (shaft 6), while the P type and D type utilise body turn.

To be more precise, with the I type the pattern increases linearly in the back-swing. At the top position it is great in both the +H and +V directions, and the down-swing is entered in that state. It is characterized by a relatively narrow pattern. This type of swing is common in golfers who have a strong wrist turn and utilize only one direction (axis) of the golf club 2.

Other characteristics are:

Utilizing the rebound of the golf club 2 (shaft 6) in the take-back to swing.

A tendency for the hands and body to have simultaneous timing on impact: in other words, the H and V strain waveforms are the same.

A tendency to make frequent use of wrist-turn between top and impact.

Common in hook-grip golfers (mainly left-handed).

Impact is relatively level.

The P type falls into two sub-types represented respectively by the unbroken and broken lines in FIG. 7. With the type represented by the unbroken line, great strain is generated in the +V direction at top position, and in the +H direction continuously from body-turn. With the type represented by the broken line, strain in the +V direction at top position is relatively small, but is generated in the V direction after entering the down-swing action, and in the H direction as a result of body-turn.

With this type of swing, cocking is released early in the down-blow, wrist-turn is implemented, and strain is small in the −V and +H directions immediately before impact.

Other characteristics are:

Slow take-back, with relatively great reserve at top.

A tendency to make frequent use of wrist-turn between top and impact.

Fairly common in hook-grip golfers (mainly right-handed).

Swing hitter type.

Impact is relatively level.

The D type falls into two sub-types represented respectively by the unbroken and broken lines in FIG. 7. With the type represented by the unbroken line, great strain is generated in the +V direction at top position, and in the +H direction continuously from body-turn. With the type represented by the broken line, strain in the +V direction at top position is relatively small, but is generated in the V direction after entering the down-swing action, and in the H direction as a result of body-turn.

Meanwhile, great strain is generated in the +V direction at top position, and in the +H direction continuously from body-turn. With this type of swing, there is little wrist-turn is implemented, and strain is relatively great in the −V and +H directions immediately before impact.

Other characteristics are:

Slow take-back, with relatively great reserve at top.

No cocking, no release.

Common in square-grip golfers.

Hard hitter type.

Upright swing, with easy vertical movement.

With the J type, strain in the +V direction at top position is great, and the cocked state is retained as the down-swing is entered. Moreover, cocking is released late in the down-blow, wrist-turn is implemented, and strain is relatively great in the −V and +H directions.

Other characteristics are:

Utilising the rebound of the golf club 2 (shaft 6) in the take-back to swing.

Cocked, delayed-release type.

Common in square-grip golfers.

Punch shots frequent, with short swing time.

Extremely upright swing, with easy vertical movement.

The H-V graph illustrated in FIG. 6 is an irregular type according to the above classification, and might be called a D-J type.

Figure 8:
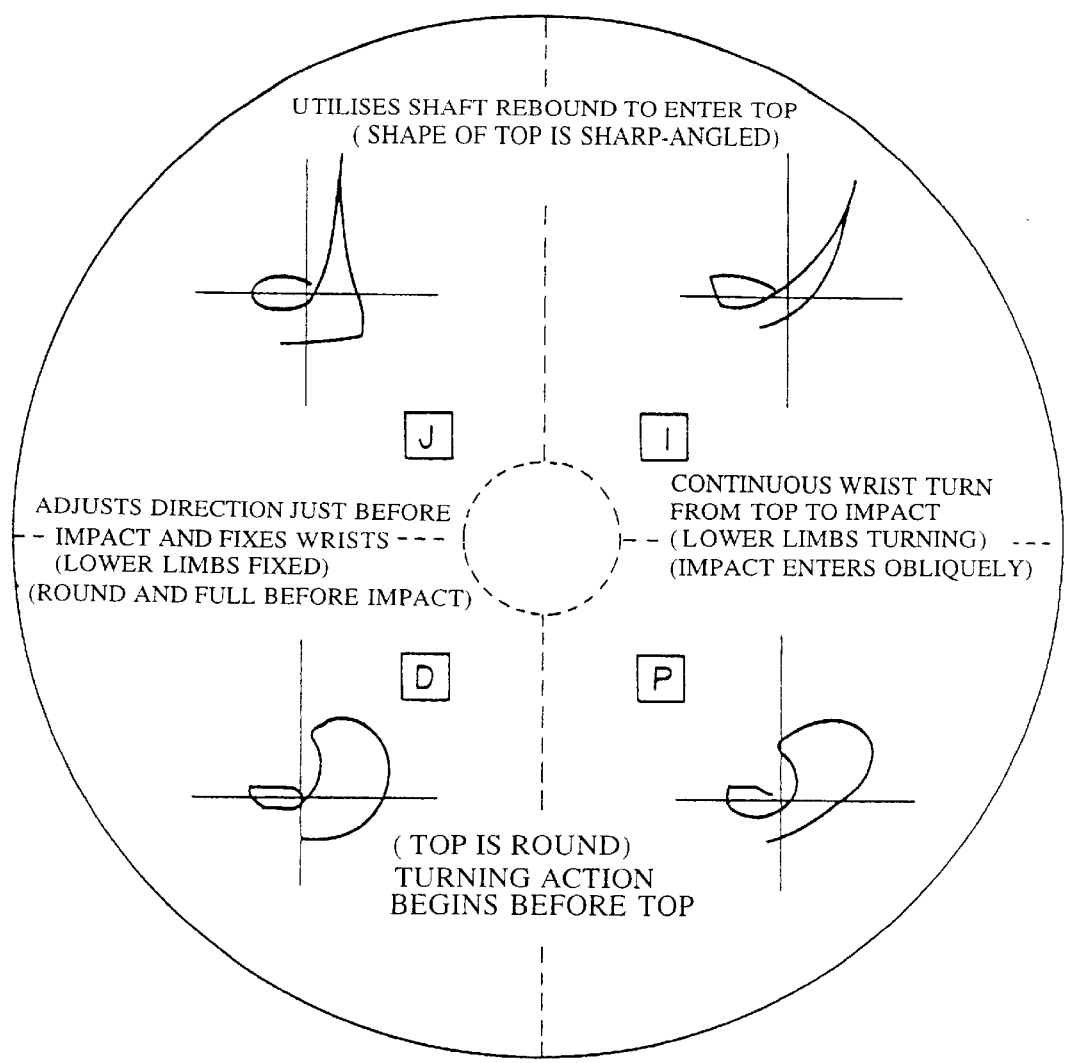
FIG. 8 is an explanatory drawing designed to illustrate the correlation between the various types in a manner which is simple to understand in the abovementioned golf swing analyzer 1.

FIG. 8 follows the above analysis further, and is an explanatory drawing designed to illustrate the correlation between the various types in a manner which is simple to understand. The various types have certain points in common. That is to say, the I and J types share sharp-angled tops, while in the I and P types the impact enters obliquely. The P and D types both have round tops, and the D and J types are round and full before impact.

With the I type, the top is cut back by the rebound of the shaft, and lower limbs turn does not stop on impact.

The P type shifts to a continuous turning action at the top, and lower limbs turn does not stop on impact.

The D type, shifts to a continuous turning action at the top, and lower limbs turn stops on impact.

With the J type, the top is cut back by the rebound of the shaft, and lower limbs turn stops on impact.

The types can also be classified by cut-back at the top of the swing and by the phase angle immediately prior to impact (difference in strain acceleration between hand action (V axis) and body turning action (H axis)).

In other words, in the case of the I and J types the phase angle (relative phase angle) $\Theta 1$ of cut-back from the top is smaller than 18°, whereas it is greater than 18° in the case of P and D types.

Meanwhile, the phase angle immediately prior to impact (mean phase angle during 30 ms of time) $\Theta 2$ is smaller than 33° in the D and J types, while it is greater than 33° in the case of I and P types.

The angle of tangency (phase=0) of the H-V graph is 45° in the case of golfers whose hand and body turn actions are simultaneous, greater than 45° if hand action is swifter than body turn action, and smaller than 45° if body turn action is swifter than hand action.

As has been explained above, a golfer's swing as such is unconnected with experience or technique, or with proficiency, age or sex, and can be classified broadly into the four abovementioned types. As a result of painstaking research and experiments with a view to providing easily, speedily and objectively a golf club shaft which is suited to each of these types, the inventors of the present invention have made the following discovery.

Namely, it has become evident that golf club shafts suited to these four types can be classified not by flex as hitherto, but by twist torque and kick point.

Twist torque (or just 'torque') signifies the force exerted on the golf club shaft in the direction of twist around the axis, and as will be explained below, is normally represented by the angle of twist.

Kick point can be likened to the center point in the swing of the golf club shaft, and as will be explained below, is generally represented by the ratio (%) of length from the grip end.

Figure 9:
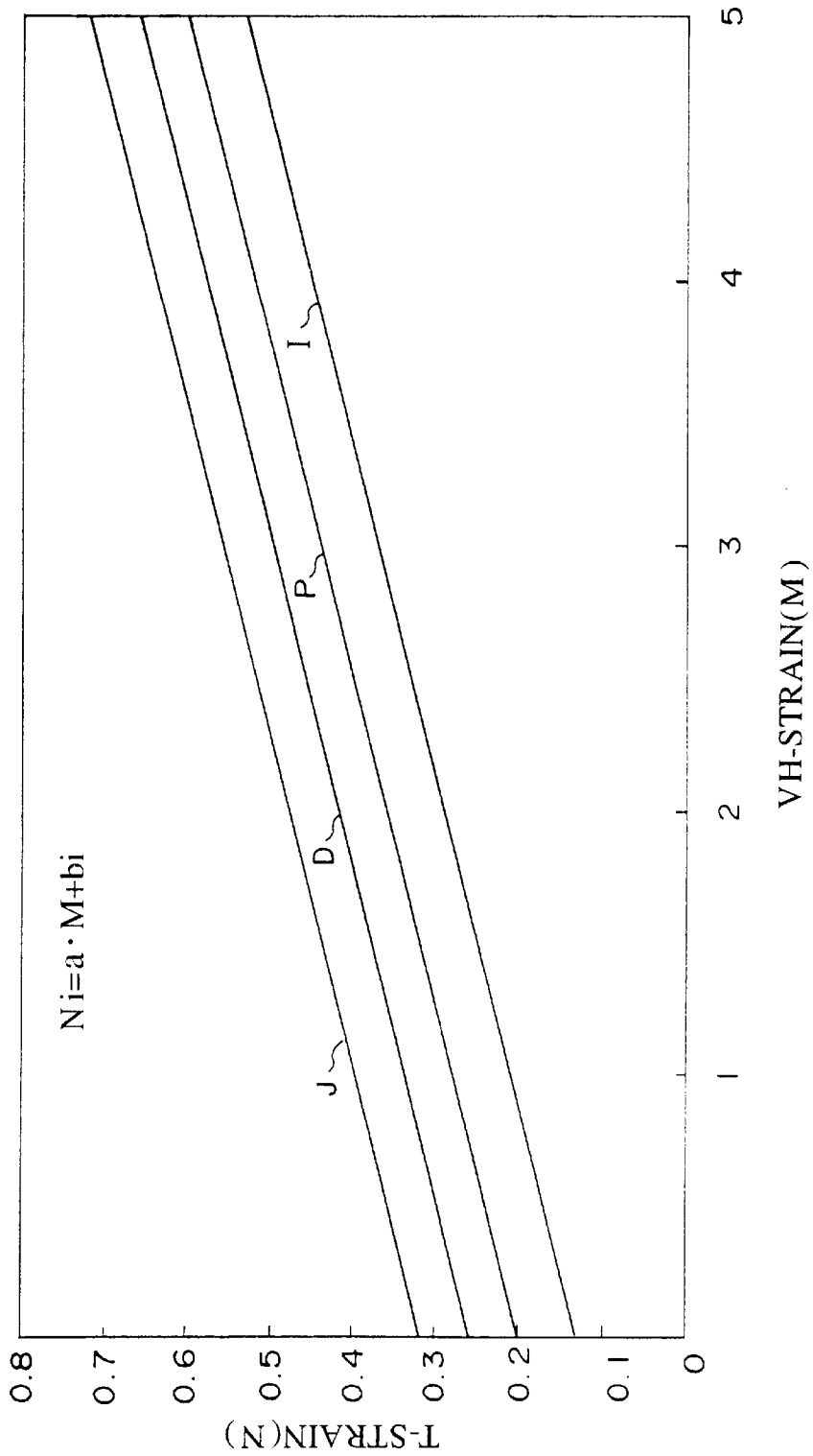
FIG. 9 is a graph illustrating the relationship of measurement values for twist strain to VH strain in the golf club shaft to which the present invention pertains.

FIG. 9 is a graph illustrating the relationship of measurement values for twist strain to VH strain in the golf club shaft to which the present invention pertains, and shows that the I type, P type, D type and J type are each on specific lines.

The VH strain referred to here is a value in the striking direction or in the direction at right-angles to the striking direction, whichever is the greater, based on the detection signals from the first and second strain gauges. This value will be called M, while the measurement values of twist strain for each type will be called Ni (i=I-type shaft, P-type shaft, D-type shaft and J-type shaft). If, then, a is a constant, and bi is a constant for each type, the formula $$Ni = a \cdot M + bi \qquad \ldots \text{Formula (1)}$$

obtains.

Figure 10:
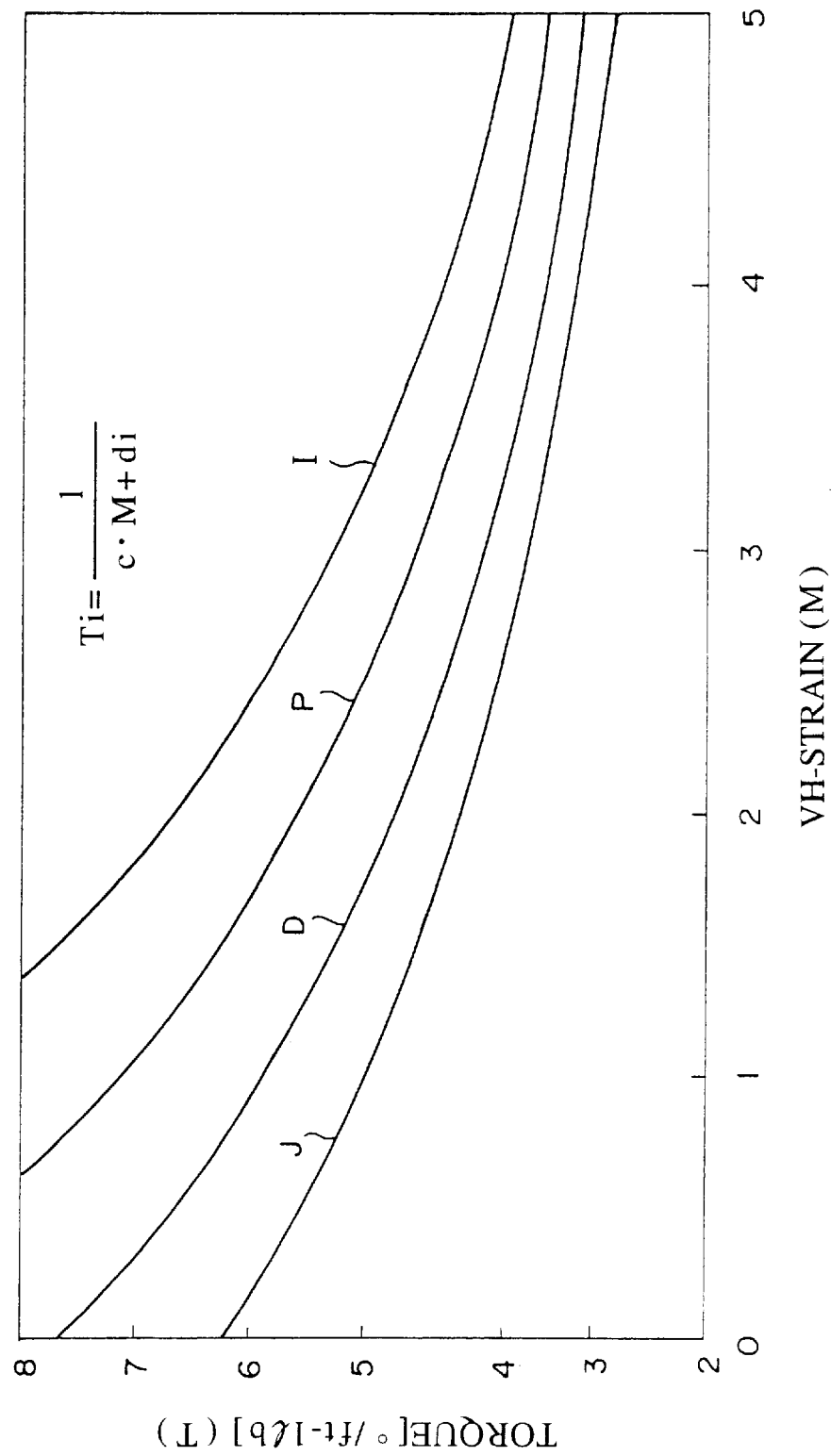
FIG. 10 is a graph illustrating the relationship of torque to VH strain in the golf club shaft to which the present invention pertains.

FIG. 10 is a graph illustrating the relationship of torque to VH strain in the golf club shaft to which the present invention pertains, and shows that the I type, P type, D type and J type are each on specific curves.

If Ti represents the torque for each type, M represents the VH strain value, c is a constant, and di is a constant for each type, the formula $$Ti = 1/(c \cdot M + di) \qquad \ldots \text{Formula (2)}$$

obtains.

Figure 11:
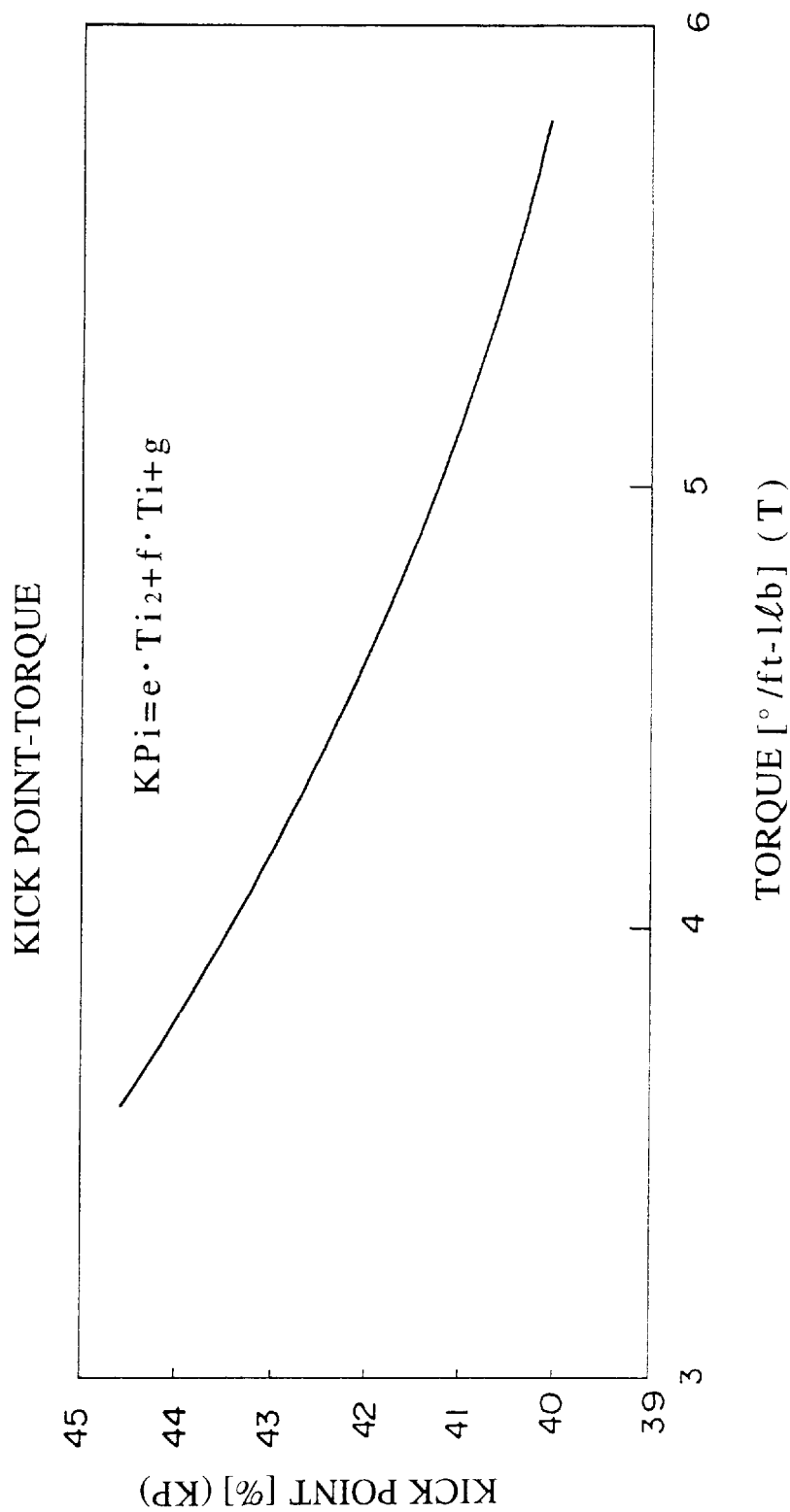
FIG. 11 is a graph illustrating the relationship of the kick point to torque in the golf club shaft to which the present invention pertains.

FIG. 11 is a graph illustrating the relationship of the kick point to torque in the golf club shaft to which the present invention pertains, and shows that the I type, P type, D type and J type are on the same curve.

If KPi represents the kick point for each type, Ti represents the torque for each type, and e, f and g are constants, the formula $$KPi = e \cdot Ti^2 + f \cdot Ti + g \qquad \ldots \text{Formula (3)}$$

obtains.

Figure 12:
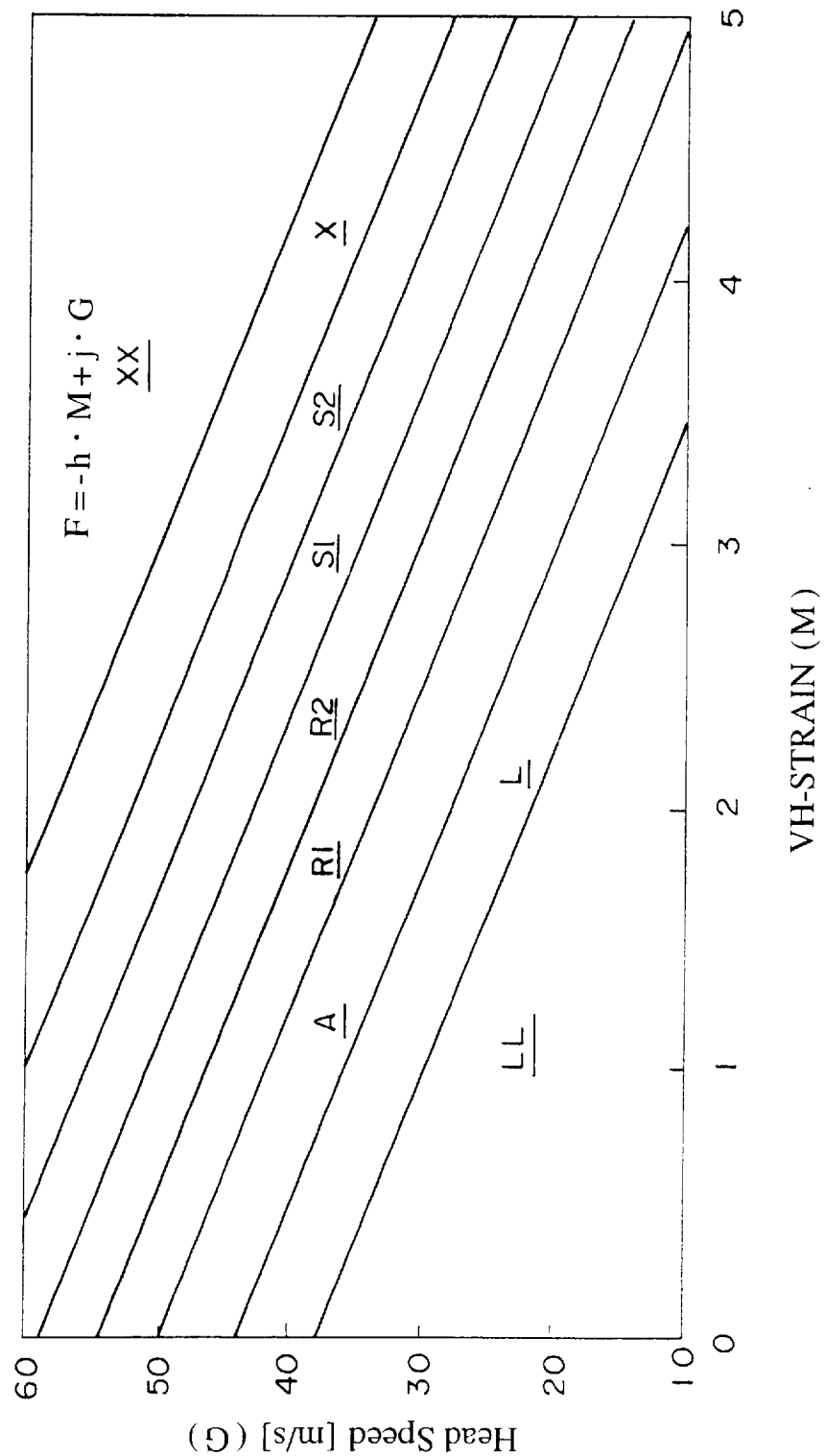
FIG. 12 is a graph illustrating the relationship of head speed to VH strain in the golf club shaft to which the present invention pertains.

FIG. 12 is a graph illustrating the relationship of head speed to VH strain in the golf club shaft to which the present invention pertains, and demonstrates that the conventional flexes LL, L, A, R1, R2, S1, S2, X and XX are each within a range demarcated by specific lines.

If F represents the flex, G represents the head speed, and h and j are constants, the formula $$F = -h \cdot M + j \cdot g \qquad \ldots \text{Formula (4)}$$

obtains.

From measurements and analyses such as the above, the present invention allows golf club shafts suited to each of the types I, P, D and J to be prepared by selecting twist torque and kick point.

FIG. 13 is a table illustrating the relationship between golf club shafts (referred to in the drawing and hereafter simply as I, P, D and J) for use by the various types (I type, P type, D type and J type) on the one hand, and torque and kick point.

It is desirable that the torque on the golf club shaft I is comparatively great, becoming smaller in the order I, P, D, J.

Meanwhile, it is desirable that the kick point on the golf club shaft I is comparatively small (the tip), becoming greater (the butt) in the order I, P, D, J.

FIG. 14 is a table illustrating in the form of concrete figures the relationship between golf club shafts for use by the various types (I type, P type, D type and J type) on the one hand, and torque, kick point and flex on the other, while FIG. 15 is a table showing concrete figures for flex. It may be added that the figures quoted within parentheses in FIG. 14 demonstrate the range of adjustment in accordance with the length of the shaft, while those outside the parentheses refer to the current mean shaft length of 45 inches (1143 mm).

As may be seen from the drawing, the torque in the case of the I-type shaft is 5.6–7.2°, and 5.8° where the shaft is of average length.

The torque in the case of the P-type shaft is 4.6–5.0°, and 4.8° where the shaft is of average length.

The torque in the case of the D-type shaft is 4.0–4.4°, and 4.2° where the shaft is of average length.

The torque in the case of the J-type shaft is 3.4–3.8°, and 3.6° where the shaft is of average length.

Similarly, the kick point in the case of the I-type shaft is 38–42%, and 40.0% where the shaft Is of average length.

The kick point In the case of the P-type shaft is 40–43%, and 41.5% where the shaft is of average length.

The kick point in the case of the D-type shaft is 42–45%, and 43.0% where the shaft is of average length.

The kick point In the case of the J-type shaft is 44–47%, and 44.5% where the shaft is of average length.

Meanwhile, as will be seen from FIG. 15, the flex is 150 in the case of the most pliable A type, 133 in the case of the R1 type, 132 in the case of the R2 type, 126 in the case of the S1 type, 120 in the case of the S2 type, and 112 in the case of the X type.

Next, outline descriptions of the abovementioned torque, kick point and flex measurement testing apparatus will be given. The above values are all based on the apparatus as described below.

Figure 16:
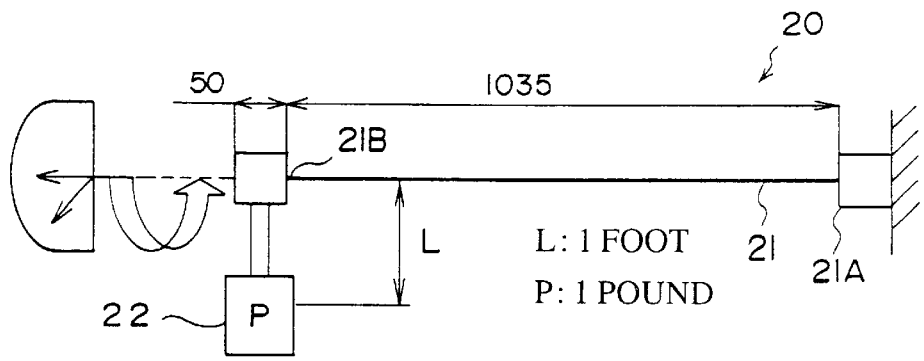
FIG. 16 is an outline explanatory diagram illustrating the torque measurement testing apparatus 20 in the golf club shaft to which the present invention pertains.

FIG. 16 is an outline explanatory diagram illustrating the torque measurement testing apparatus 20. The butt 21A of the golf club shaft 21 is fixed, and a weight 22 is hung on the tip 21B. The turn angle is measured when [the shaft] is twisted, and the turn angle per unit length and weight is taken as the torque value.

Figure 17:
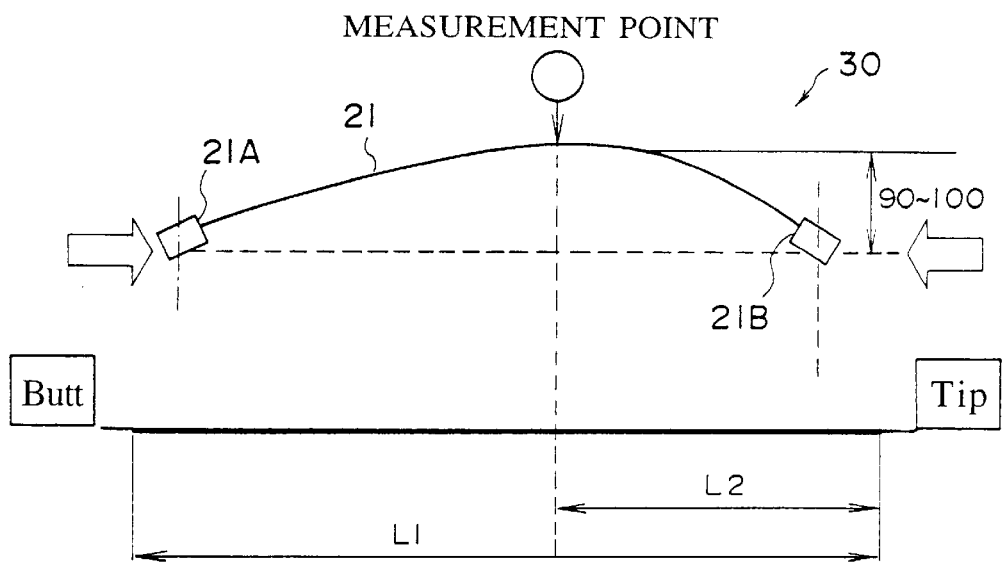
FIG. 17 is an outline explanatory diagram illustrating the kick point measurement testing apparatus 30 in the golf club shaft to which the present invention pertains.

FIG. 17 is an outline explanatory diagram illustrating the kick point measurement testing apparatus 30. Loads are applied from the butt 21A and tip 21B of the golf club shaft 21 in the direction of each other. The maximum distance L2 is measured when the shaft has bent 90–100 mm from its initial position, and L2 / L1 100% is taken as the kick point value.

Figure 18:
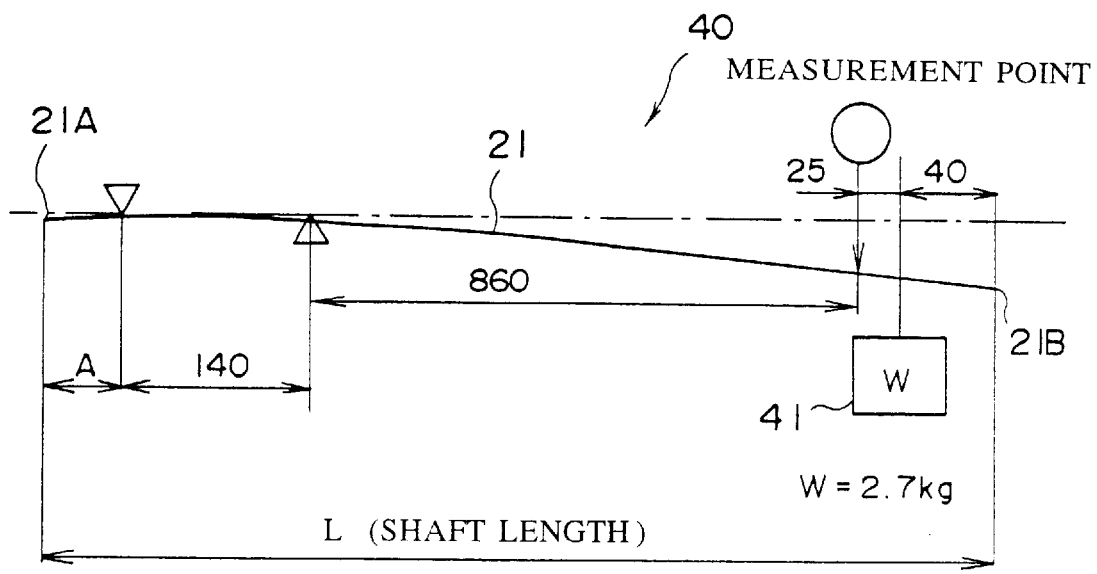
FIG. 18 is an outline explanatory diagram illustrating the flex measurement testing apparatus 40 (sequential type) in the golf club shaft to which the present invention pertains.

FIG. 18 is an outline explanatory diagram illustrating the flex measurement testing apparatus 40 (sequential type). The butt 21A end of the golf club shaft 21 is supported upwards and downwards in two separate positions, whereupon a weight 41 is hung on the tip 21B end and the amount of deviation is taken as the flex value.

Figure 19:
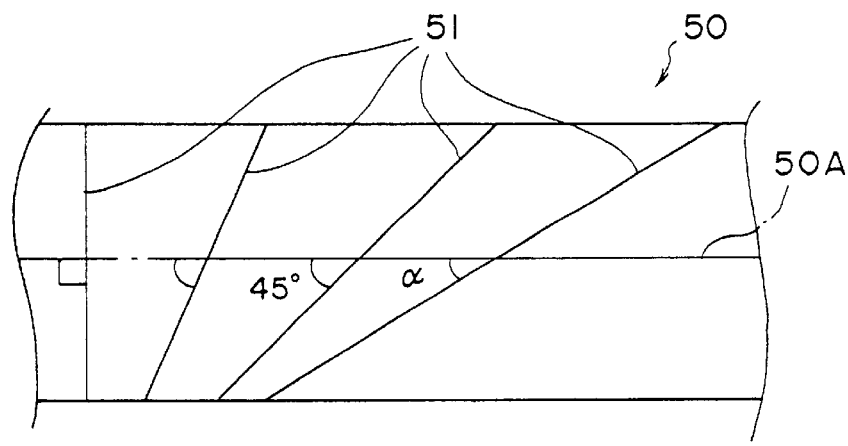
FIG. 19 is an explanatory diagram depicting the angle of orientation a of the fibers in the material when the golf club shaft 50 to which the present invention pertains is manufactured from carbon fiber reinforced plastics or glass fiber reinforced plastics.

FIG. 19 is an explanatory diagram depicting the angle of orientation $\alpha$ of the fibers in the material when the golf club shaft 50 to which the present invention pertains is manufactured from carbon fiber reinforced plastics or glass fiber reinforced plastics.

Stiffness in twist and stiffness in bend both reach their maximum when the winding direction of the fibers 51 is inclined at 45° to the axis 50A of the golf club shaft 50.

Torque is greatest when the angle of orientation $\alpha$ is 45°, and decreases with distance from this angle.

The kick point is linked to the degree of stiffness in bend which is applied to various parts of the golf club shaft 50.

Figure 20:
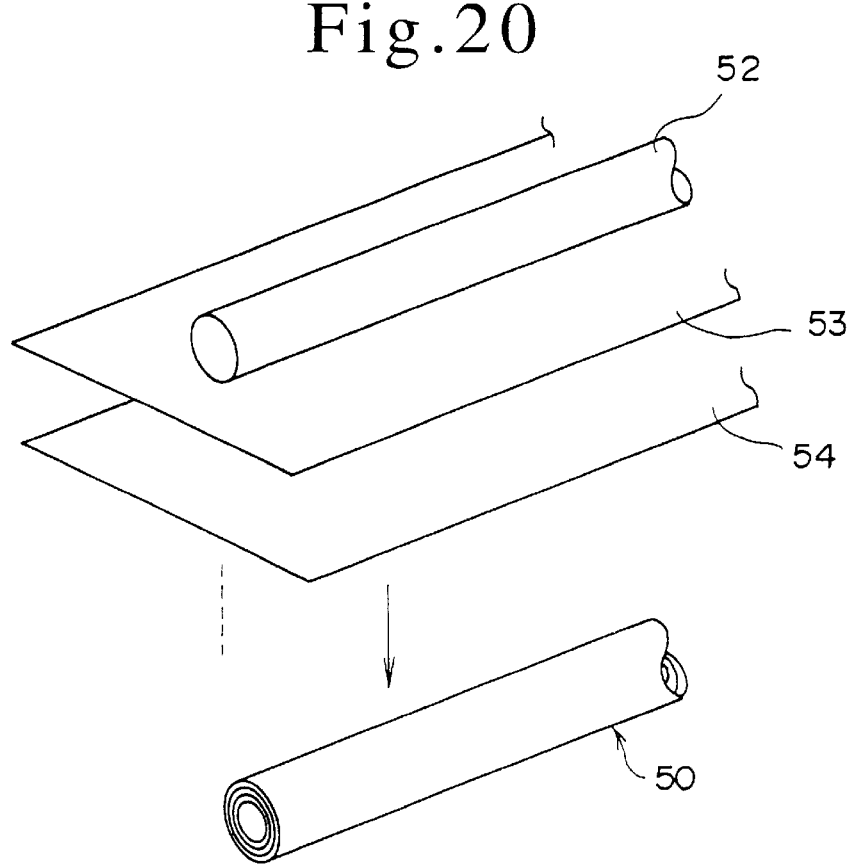
FIG. 20 is an oblique view illustrating part of the process of forming the golf club shaft 50 to which the present invention pertains by winding a plurality of layers of fiber sheeting 53, 54 . . . around a metal core 52 and applying heat.

FIG. 20 is an oblique view illustrating part of the process of forming the golf club shaft 50 to which the present invention pertains by winding a plurality of layers of fiber sheeting 53, 54 . . . around a metal core 52 and applying heat. Since the fiber sheeting 53, 54 . . . is classified by units of density when supplied, during actual manufacture this fiber sheeting 53, 54 . . . is selected as suitable and combined to determine the characteristics of the golf club shaft 50.

FIG. 21 Is a graph showing EI distribution against the length of the golf club shaft 50, where E Is Young's modulus and I Is the moment of Inertia.

As the drawing shows, the characteristic curve in the longitudinal direction differs between the I-type, P-type, D-type and J-type shafts, and the respective kick points assume the length (%) of the section In the characteristic curve where the tangential gradient changes most sharply.

Consequently, In the manufacture of the golf club shaft 50 the characteristics shown In FIG. 21 are achieved by suitably selecting the type of fiber, diameter, angle of orientation $\alpha$, type of fiber sheeting 53, 54 . . . number of layers and other factors.

Thus, it is possible to provide, in the form of I-type, P-type, D-type and J-type shafts, four types of shaft with differing distributions of stiffness of twist and stiffness of bend by keeping the flex at the same standard and adjusting the torque and kick point.

In this manner, the present invention specifies golf club shafts by employing torque and kick point to classify them on the basis of patterns of golfers' swings, thus making it possible to select shafts objectively according to each golfer's swing pattern or type.

What is claimed is:

1. A method of classifying a golf club shaft, wherein the golf club shaft comprises:

a first strain gauge attached to a first side of said shaft facing a striking direction configured to detect a strain H in the striking direction of said shaft;

a second strain gauge attached to a second side of said shaft facing an address direction at right-angles to the striking direction configured to detect a strain V in the address direction of said shaft;

a third strain gauge configured to measure a twist of said shaft;

said shaft comprising:

detecting signals from the first strain gauge, the second strain gauge and the third strain gauge;

generating an H-V graph on rectangular coordinates with the strain H in the striking direction and the strain in the addressing direction being combined; and classifying the shaft into four types, an I-type shaft, a P-type shaft, a D-type shaft and a J-type shaft, each having a torque, according to the H-V graph associate with a swing of a golfer;

wherein the torque of said I-type shaft is between 5.6° and 7.2°, the torque of said P-type shaft is between 4.6° and 5.0°, the torque of said D-type shaft is between 4.0° and 4.4°, and the torque of said J-type shaft is between 3.4° and 3.8°.

2. A method classifying a golf club shaft according to claim 1, wherein said kick point is increased gradually in order from said I-type shaft through said P-type shaft and said D-type shaft to said J-type shaft.

3. A method of classifying a golf club shaft according to claim 1, wherein said shaft is manufactured from carbon fiber reinforced plastics or glass fiber reinforced plastics.

4. The method of claim 1, wherein the torque of the I-type shaft is 5.8°.

5. The method of claim 1, wherein the torque of the P-type shaft is 4.8°.

6. The method of claim 1, wherein the torque of the D-type shaft is 4.2°.

7. The method of claim 1, wherein the torque of the J-type shaft is 3.6°.

8. A method of classifying a golf club shaft, wherein the golf club shaft comprises:

a first strain gauge attached to a first side of said shaft facing a striking direction configured to detect a strain H in the striking direction of said shaft;

a second strain gauge attached to a second side of said shaft facing an address direction at right-angles to the striking direction configured to detect a strain V in the address direction of said shaft;

a third strain gauge configured to measure a twist of said shaft;

said method comprising:

detecting signals from the first strain gauge, the second strain gauge and the third strain gauge;

generating an H-V graph on rectangular coordinates with the strain H in the striking direction and the strain in the addressing direction being combined; and classifying the shaft into four types, an I-type shaft, a P-type shaft, a D-type shaft and a J-type shaft, each having a kick point, according to the H-V graph associated with a golfer;

wherein the kick point of said I-type shaft is between 38% and 42%, the kick point of said P-type shaft is between 40% and 43%, the kick point of said D-type shaft is between 42% and 45%, and the kick point of said J-type shaft is between 44% and 47%.

9. A method of classifying a golf club shaft according to claim 8, wherein said torque is reduced gradually in order from said I-type shaft through said P-type shaft and said D-type shaft to said J-type shaft.

10. The method of claim 8, wherein the kick point of the I-type shaft is 40%.

11. The method of claim 8, wherein the kick point of the P-type shaft is 41.5%.

12. The method of claim 8, wherein the kick point of the D-type shaft is 43%.

13. The method of claim 8, wherein the kick point of the J-type shaft is 44.5%.

14. A method of classifying a golf club shaft according to claim 8, wherein said shaft is manufactured from carbon fiber reinforced plastics or glass fiber reinforced plastics.

15. A method of classifying a golf club shaft, wherein the golf club shaft comprises:

a first strain gauge attached to a first side of said shaft facing a striking direction configured to detect a strain H in the striking direction of said shaft;

a second strain gauge attached to a second side of said shaft facing an address direction at right-angles to the striking direction configured to detect a strain V in the address direction of said shaft;

a third strain gauge configured to measure a twist of said shaft;

said method comprising:

detecting signals from the first strain gauge, the second strain gauge and the third strain gauge;

generating an H-V graph on rectangular coordinates with the strain H in the striking direction and the strain in the addressing direction being combined; and classifying the shaft into four types, an I-type shaft, a P-type shaft, a D-type shaft and a J-type shaft, each having a torque and a kick point, according to the H-V graph associated with a golfer;

wherein the torque of said I-type shaft is between 5.6° and 7.2°, the torque of said P-type shaft is between 4.6° and 5.0°, the torque of said D-type shaft is between 4.0° and 4.4°, and the torque of said J-type shaft is between 3.4° and 3.8°, and the kick point of said I-type shaft is between 38% and 42%, the kick point of said P-type shaft is between 40% and 43%, the kick point of said D-type shaft is between 42% and 45%, and a kick point of said J-type shaft is between 44% and 47%.

16. A method of classifying a golf club shaft according to claim 15, wherein said shaft is manufactured from carbon fiber reinforced plastics or glass fiber reinforced plastics.

17. The method of claim 15, wherein the torque of the I-type shaft is 5.8°.

18. The method of claim 15, wherein the torque of the P-type shaft is 4.8°.

19. The method of claim 15, wherein the torque of the D-type shaft is 4.2°.

20. The method of claim 15, wherein the torque of the J-type shaft is 3.6°.

21. The method of claim 15, wherein the kick point of the I-type shaft is 40%.

22. The method of claim 15, wherein the kick point of the P-type shaft is 41.5%.

23. The method of claim 15, wherein the kick point of the D-type shaft is 43%.

24. The method of claim 15, wherein the kick point of the J-type shaft is 44.5%.

* * * * *